United States Patent [19]

Dahl et al.

[11] Patent Number: 5,074,313
[45] Date of Patent: Dec. 24, 1991

[54] POROUS ELECTRODE WITH ENHANCED REACTIVE SURFACE

[75] Inventors: Roger W. Dahl, Andover; Sanjiv Arora, New Brighton, both of Minn.

[73] Assignee: Cardiac Pacemakers, Inc., St. Paul, Minn.

[21] Appl. No.: 512,651

[22] Filed: Apr. 20, 1990

Related U.S. Application Data

[63] Continuation-in-part of Ser. No. 325,764, Mar. 20, 1989, abandoned.

[51] Int. Cl.$^5$ ............................................. A61N 1/05
[52] U.S. Cl. ................................. 128/784; 128/786; 128/798; 128/419 P; 128/419 D
[58] Field of Search ............................. 128/784–786, 128/642, 419 P, 419 D, 798

[56] References Cited

U.S. PATENT DOCUMENTS

| | | | |
|---|---|---|---|
| 4,011,861 | 3/1977 | Enger. | |
| 4,156,429 | 5/1979 | Amundson | 128/419 D |
| 4,280,514 | 7/1981 | MacGregor. | |
| 4,281,668 | 8/1981 | Richter et al. | 128/784 |
| 4,281,669 | 8/1981 | MacGregor. | |
| 4,407,302 | 10/1983 | Hirshorn et al. | 128/784 |
| 4,408,604 | 10/1983 | Hirshorn et al. | 128/785 |
| 4,444,206 | 4/1984 | Gold | 128/784 |
| 4,542,752 | 9/1985 | DeHaan et al. | 128/784 |
| 4,577,642 | 3/1986 | Stokes | 128/784 |
| 4,603,704 | 8/1986 | Mund et al. | 128/784 |
| 4,611,604 | 9/1986 | Botvidsson et al. | 128/784 |
| 4,612,100 | 9/1986 | Edeling et al. | 128/784 X |
| 4,773,433 | 9/1988 | Richter et al. | 128/784 |
| 4,784,159 | 11/1988 | Szilagyi | 128/784 |
| 4,784,160 | 11/1988 | Szilagyi | 128/784 |
| 4,784,161 | 11/1988 | Skalsky et al. | 128/785 |
| 4,819,662 | 4/1989 | Heil, Jr. et al. | 128/786 |
| 4,827,932 | 5/1989 | Ideker et al. | 128/419 D |
| 4,844,099 | 7/1989 | Skalsky et al. | |
| 4,936,317 | 6/1990 | MacGregor. | |
| 5,020,544 | 6/1991 | Dahl et al. | 128/784 |

FOREIGN PATENT DOCUMENTS

| | | |
|---|---|---|
| A10054781 | 6/1982 | European Pat. Off. . |
| A10085743 | 8/1982 | European Pat. Off. . |
| 0064289 | 11/1982 | European Pat. Off. . |
| A20312495 | 9/1984 | European Pat. Off. . |

Primary Examiner—Lee S. Cohen
Attorney, Agent, or Firm—Haugen and Nikolai

[57] ABSTRACT

A body implantable electrode includes a platinum wire or filament compressed and bundled into a serpentine configuration and retained within a platinum screen, thus to form a highly porous electrode. The electrode body is then surface treated by vapor deposition or vapor deposition in combination with electroplating, to provide an adhesion layer, a texturizing layer, and one or more catalytic cover layers. The texturizing layer, which can be titanium, carbon black or aluminum, is formed with multiple nodules and depressions which substantially increase the reactive surface area of the electrode. The catalytic layer can be platinum, platinum-black or platinum followed by a layer of carbon. The combination of macro porosity and micro texture provides an electrode that promotes tissue ingrowth after implant and maintains a low chronic stimulation threshold due to its large reactive surface area in proportion to its geometric size.

27 Claims, 2 Drawing Sheets

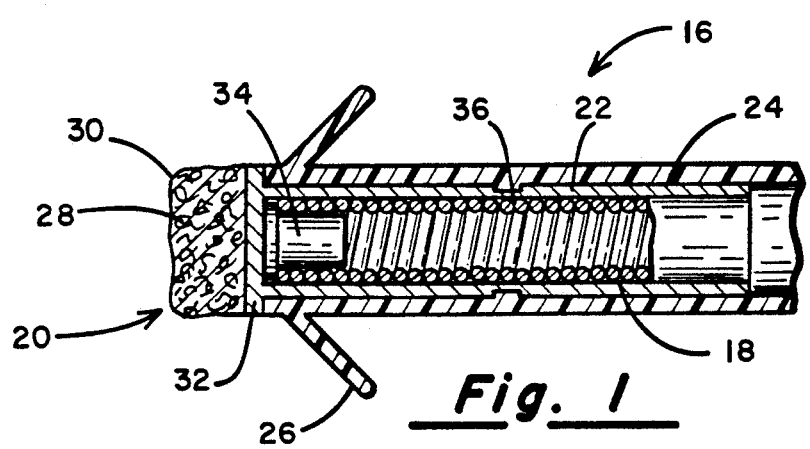
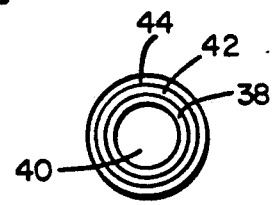
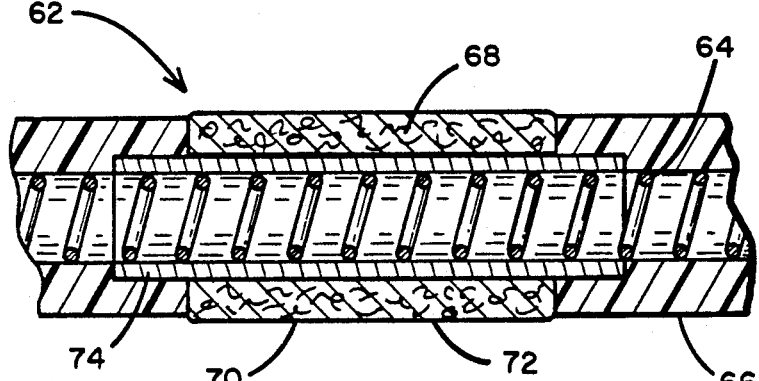
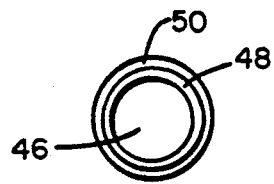
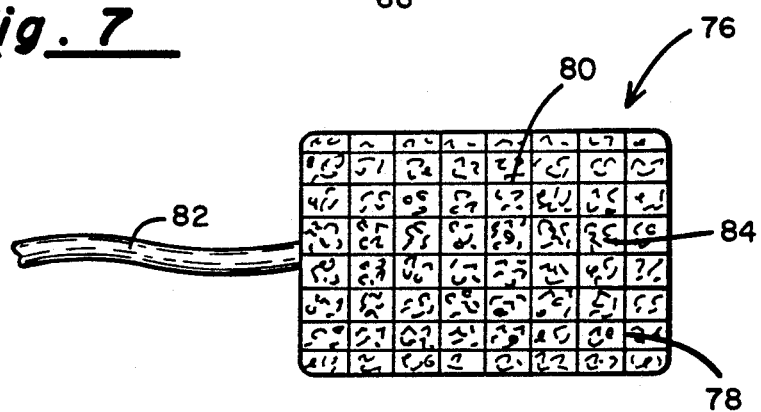
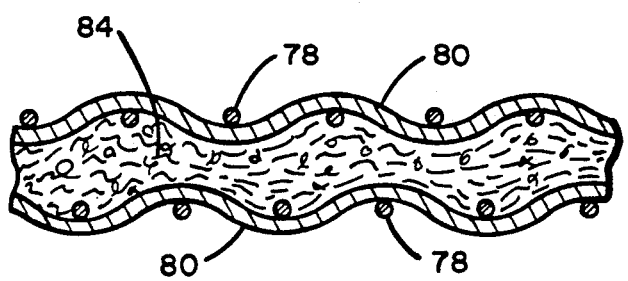
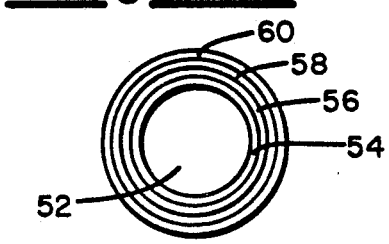

POROUS ELECTRODE WITH ENHANCED REACTIVE SURFACE

CROSS-REFERENCE TO RELATED APPLICATION

This is a Continuation-in-Part application of application Ser. No. 07/325,764, filed Mar. 20, 1989, now abandoned.

BACKGROUND OF THE INVENTION

This invention relates to body implantable medical devices, and more particularly to implantable electrodes for sensing electrical impulses in body tissue or for delivering electrical stimulation pulses to an organ, for example for pacing the heart or arresting tachycardia or cardioversion.

Cardiac pacing leads are well known and widely employed for carrying pulse stimulation signals to the heart from a battery operated pacemaker or other pulse generating means, as well as for monitoring electrical activity of the heart from a location outside of the body. More recently, electrodes have been used to stimulate the heart in an effort to terminate tachycardia or other arrhythmias. In all of these applications, it is highly desirable to minimize the electrical impedance at the interface between the electrode and body tissue.

A direct approach to reducing interface impedance is to increase the electrode surface area, which is subject to practical limits for maximum electrode size. Increasing the number of reactive sites in a electrode improves its ability to convert an electronic current to an ionic current. As used in this application, the term "impedance" relates to the conversion of electronic Current to ionic current.

One particularly effective means of increasing reactive surface area is to form a highly porous electrode body, for example as disclosed in U.S. Pat. No. 4,011,861 (Enger), and in U.S. Pat. No. 4,156,429 (Amundson). The Amundson Patent discloses a porous electrode formed by a bundle of fibers, preferably of platinum but alternatively of Elgiloy, titanium, or a platinum iridium alloy. The fibers are compressed into a bundle, then heated to a sufficient temperature and for a sufficient time to sinter the fibers. The fibers or filaments may be bundled within a metallic screen or grid, and preferably form between about three percent and thirty percent of the electrode volume, with the balance of the volume open. This macro porosity enhances ingrowth of tissue to stabilize the electrode, and the increased surface area to volume ratio lowers interface impedance, improving both sensing and pacing performance.

Other approaches to increasing electrode efficiency concern reducing fibrosis, i.e. formation of a capsule of inactive tissue that surrounds and isolates the electrode from active tissue. The resultant increase in distance from the electrode to viable tissue increases the voltage required to generate the same transmembrane potential. In U.S. Pat. No. 4,281,668 (Richter et al), a vitreous carbon or pyrolytic carbon electrode is superficially activated, e.g. by oxidation, for micro porosity. The electrode then is coated with a body compatible, ion conducting and hydrophobic plastic. This approach is said to substantially prevent thrombus formation.

U.S. Pat. No. 4,603,704 (Mund et al) discloses an electrode including a hemispherical head of platinum or titanium. A porous layer is coated over the head, either by vapor deposition or by magnetron sputtering. The porous layer consists of a carbide, a nitride or a carbonitride of at least one of the following metals: titanium, vanadium, zirconium, niobium, molybdenum, hafnium, tantalum or tungsten.

U.S. Pat. No. 4,542,752 (DeHaan et al) features an implantable lead with a core of platinum, titanium or similar metal, covered with a porous sintered titanium alloy, which in turn is covered with a porous carbon lattice. The porous carbon surface is said to promote tissue ingrowth and provide low polarization impedance.

In U.S. Pat. No. 4,407,302 (Hirshorn et al), the external surface of a cardiac pacer electrode tip is provided with a concavity and roughened over its exterior, for example by abrading with a jet of glass beads, to increase the micro surface area of the electrode tip and reduce the sensing impedance of the tip. At the same time, the concave area in an otherwise convex surface of the electrode tip is said to significantly and advantageously increase the pacing impedance. The underlying theory of this approach, with respect to pacing impedance, is that higher resistance reduces the current flow for a given voltage, and consequently reduces the energy involved in pacing.

An example of a porous electrode tip is found in U.S. Pat. No. 4,577,642 (Stokes), in which the electrode is formed by sintering spheres or other particles of metal resulting in formation of molecular sieves which control the elution rate of a drug housed in the lead distal end. This approach, however, requires a balancing between a relatively large reactive surface area and pore size of the structure. Sintering small spheres enhances surface area but reduces porosity. Conversely, sintering of larger spheres results in a more porous structure with lower surface area. In any event, maximum theoretical porosity is under fifty percent, and the pores or passages typically are tortious and convoluted.

Despite the varying degrees of success of the above approaches, polarization losses and after potentials remain significant problems to electrode efficiency. Depending on applied potential and pulse duration, activities at the electrode interface range from reorganization of ions to electrolysis. As current densities increase, these reactions change the ionic concentration at the interface, requiring migration of ions from increasingly greater distances. The energy required to reorient and move the ions is the measure of the polarization loss of the electrode, and represents wasted energy for a loss in efficiency. The source of the after potential is the concentration gradient or residual charge at the end of a pulse.

Therefore, it is an object of the present invention to provide a body implantable electrode with substantially reduced polarization loss, and reduced capacitive coupling at the electrode/tissue interface, thereby reducing signal distortion.

Another object is to provide an electrode construction with reduced after potential, thus reducing the refractory period and reducing sensing delays following stimulating pulses.

Another object is to provide an electrode having large, non-tortious pores open to the electrode exterior in combination with a microscopic texturing of exterior and interior surfaces of the electrode.

Yet another object is to provide an intravascular pacing lead having a reduced chronic threshold, improved pulse sensing capability and shorter recovery time for sensing after stimulation pulses.

SUMMARY OF THE INVENTION

To achieve these and other objects, there is provided a body implantable electrode. The electrode includes an electrode body constructed of an electrically conductive filament structure including a plurality of elongate fiber elements with diameters of at least five microns. The fiber elements are bundled in close proximity with one another and form multiple passages throughout the electrode body and open to the exterior of the electrode body. Thus, an exposed surface of the electrode body includes an exterior surface portion and an interior surface portion disposed along and defining the passageways. At least some of the passageways have diameters in the range of from ten to fifty microns. The volume occupied by the passageways comprises more than one half of the total volume occupied by the electrode body. The electrode further includes a surface texture comprising multiple surface irregularities formed over substantially the entire exposed surface of the electrode body. The irregularities are in sufficient size and density to substantially increase the surface area of the exposed surface, as compared to an equivalent surface area for an identically sized filament structure with a smooth, non-textured surface.

Preferably the filament structure is a single strand of platinum wire, stretched and then packed or bundled into a compress, in which case the fiber elements are portions of the length of the wire. Heat is applied to sinter parts of the wire together to form the electrode body. Titanium and platinum-iridium alloys may be used for the wire in lieu of platinum.

The surface irregularities are advantageously formed by glow discharge or vapor deposition, after the platinum wire has been sintered. In one preferred approach, an underlayer of titanium is sputtered onto the electrode body to provide the textured layer, forming multiple nodules or adhering particles. These particles are somewhat elongate and irregular, but generally have average diameters of from one to two microns. The titanium layer also provides an adhesion layer for a subsequent sputtering of platinum. The platinum layer, having a lower activation energy, is applied over the titanium to reduce the activation energy of the electrode and to improve biocompatibility. Anther metal from the platinum group (e.g. iridium, ruthenium, palladium) or an alloy of these metals, may be used in lieu of platinum. If desired, a thin carbon layer is applied over the platinum layer to further enhance biocompatibility.

A second preferred approach involves electroplating and vapor deposition. In particular, a thin underlayer of titanium is applied to the platinum electrode by vapor deposition to provide an adhesion layer for a subsequent texturizing layer, in this case platinum. The texturizing layer is formed by multiple repeated electroplating applications of platinum-black. The electrode is baked after each application to enhance adhesion of the platinum-black coating. Again, texturizing is in the form of nodules of average diameters equal to or less than about two microns.

In yet another approach, an underlayer of titanium is sputtered onto the platinum electrode body to provide an adhesion layer for subsequent sputtering of a texturizing layer of aluminum. After aluminum deposition, a platinum layer is applied over the aluminum, again to lower the activation energy and enhance biocompatibility of the electrode. If desired, a thin carbon layer is applied in this process as well.

Other approaches, satisfactory although somewhat less preferred, include a Raney platinum process whereby high energy deposition techniques ar used to impregnate the platinum electrode surface with extremely fine aluminum particles. Subsequently the aluminum particles are dissolved in an acid bath, leaving multiple, minute indentations to provide the desired surface texture.

Finally, sputter etching and sputter coating in an atmosphere that includes oxygen may serve to provide the required texture.

In any event, a salient feature of the present invention is that texture is provided not only over the electrode body exterior, but also over the interior surfaces along the passageways, so that the desired texture penetrates deeply into and throughout the electrode body. The penetrating texture yields a dramatic increase in reactive surface area, from one to two orders of magnitude greater than the equivalent reactive surface area for a nontexturized electrode. The microscopic texturing of a macroscopically porous electrode body, in accordance with the present invention, dramatically reduces the pacing impedance as well as the sensing impedance, which contradicts the theory mentioned above in connection with the Hirshorn patent. It has been found, however, that reduced pacing impedance (by elimination of polarization losses) increases the ratio of bulk impedance to the total impedance as measured between the pacing electrode and the indifferent signal return electrode. Thus, more of the voltage drop occurs across tissue, where it is useful for causing stimulation, with proportionately less of the drop occurring at the electrodes, where it is non-productive. This permits a reduction in the overall potential or pulse duration, in either event reducing the pacing energy required.

The irregularities can include multiple rises or nodules having average diameters of less than four microns, or more preferably from one to two microns as mentioned above. The surface irregularities further may include pores of approximately one micron in diameter, formed principally during the aluminum deposition step when aluminum is used to provide texture. The size of the nodules and pores, however, is not so critical as the fact that in combination they substantially increase the area of the platinum wire exposed surface by between one and two orders of magnitude, for a surprising increase in the reactive surface area of the electrode.

A substantial proportion of the passages have diameters properly sized to promote extensive fibrous ingrowth, which tends to securely anchor the implanted electrode and stabilize the electrode/tissue interface. The relatively large size of the electrode passageways further promotes use of interior electrode surfaces, as well as the exterior surface, for the conversion of an electronic current into an ionic current. This reduces polarization losses without increasing the geometric size of the electrode. In combination, the relatively large passageways to the electrode interior, and the micro texturizing of both the electrode's exterior and interior surfaces, substantially reduce electrode interface impedance for more effective stimulation pulsing and sensing of electrical pulses generated in proximate tissue.

IN THE DRAWINGS

For a better understanding of the above and other features and advantages, reference is made to the drawings in which:

FIG. 1 is a side sectional view of a cardiac pacing lead constructed in accordance with the present invention;

FIG. 2 is a photograph of a magnified image of part of an electrode of the pacing lead of FIG. 1, obtained using a scanning electron microscope;

FIG. 3 is a photograph of a further enlarged image of the electrode, again obtained with a scanning electron microscope;

FIG. 4 is a sectional view of a filament of the electrode, illustrating the layers applied to a platinum wire to provide a desired texture;

FIG. 5 is a sectional view similar to FIG. 2, illustrating an alternative texturizing approach;

FIG. 6 is a sectional view similar to that in FIG. 2, showing another alternative texturizing approach;

FIG. 7 is a side elevation of a ring electrode constructed in accordance with the present invention;

FIG. 8 is a top plan view of a patch electrode constructed in accordance with the present invention; and FIG. 9 is a side elevation of the electrode of FIG. 5.

DETAILED DESCRIPTION OF THE PREFERRED EMBODIMENTS

Turning now to the drawings, there is shown in FIG. 1 the distal end region of an implantable cardiac pacing lead 16. Devices such as lead 16 typically are inserted intravenously, for example into the subclavian vein, or the cephalic vein, and progressively moved toward the heart until the distal end reaches a selected cardiac chamber. With the distal tip positioned at a selected location, the lead proximal end, still outside the body, is maneuvered to implant the distal tip into the endocardium. The implanted lead transmits electrical signals between the selected location in the heart and the lead proximal end, for one or both of two purposes:

(a) to monitor the heart's electrical activity at the selected location; and (b) to carry stimulating signals to the selected location from a pulse generator (not shown) connected to the lead's proximal end.

To transmit the electrical signals there is provided an electrical conductor, shown in FIG. 1, as a single wound coil 18 formed of a nickel chromium alloy. The coil provides maximum flexibility for conforming to the vein, with minimal stress to the conductor. At the distal end of the lead is an electrode 20, electrically and mechanically coupled to coil 18 by a platinum alloy crimp tube 22. A flexible, dielectric sheath 24 surrounds the coil and crimp tube. The sheath is formed of a biocompatible material such as silicone rubber. A plurality of tines 26 are formed as part of sheath 24 near its distal end, and are employed to secure the lead's distal end to the selected endocardial location.

Electrode 20 is constructed of platinum o a platinum alloy, stretched to a thin wire 28, then crumpled and packed against the distal end of crimp tube 22. The wire has a diameter of at least five microns, and more preferably about 100 microns. A platinum alloy screen 30, fastened to the periphery of the crimp tube's distal end, maintains the bundled platinum alloy wire in place. The wire and screen are heated to a sufficient temperature and for a sufficient time to sinter portions of the wire and screen together, for example as explained U.S. Pat. No. 4,146,429 (Amundson), incorporated herein by reference. So constructed, electrode 20 is highly porous, for example consisting of approximately twenty percent platinum or platinum alloy by volume, and substantially the remaining eighty percent being open to permit passage of bodily fluids through electrode 20 and to promote tissue ingrowth.

Crimp tube 22 is elongate and cylindrical, with a radially outward flange 32 at its distal end to serve as an abutment for sheath 24 and an anchor for screen 30. The distal end of conductor coil 18 is retained in the crimp tube by a core pin 34 and a crimp 36 in the crimp tube wall proximally of a radially enlarged head portion of the core pin.

Figures 2, 3:
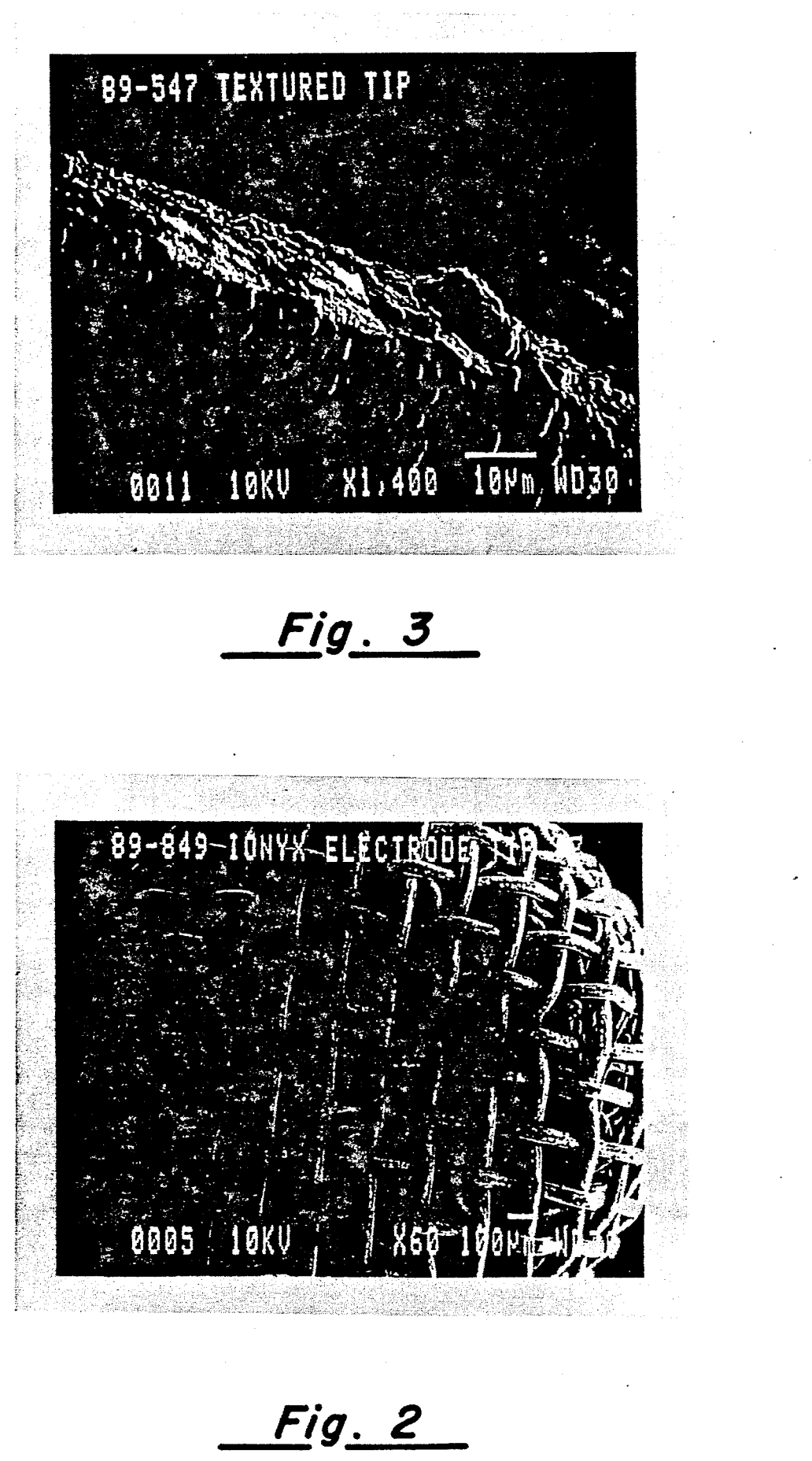

The photograph of FIG. 2 shows electrode 20 magnified sixty times, and was taken with a scanning electron microscope powered at ten kilovolts, employing secondary electron imaging. Wire 28 is surrounded by screen 30. By virtue of the screen and the sintering step, the wire is maintained in a highly serpentine winding. Nonetheless, interstitial volumetric regions of open space, between adjacent portions of wire 28, combine to form multiple open passages throughout electrode 20. Many of these passages are relatively large, for example with average diameters of thirty microns or more. A preferred range in diameters is from ten to fifty microns, although the diameters may be as large as one hundred fifty microns. Typically, the open volumetric regions comprise from seventy to ninety-five percent of the volume of electrode 20. The large proportional volume and size of the passages result in a macro porosity in electrode 20 which allows passage of bodily fluids through electrode 20 and promotes extensive tissue ingrowth.

The photograph of FIG. 3 illustrates a portion of wire 28 magnified 1,400 times with the aid of a scanning electron microscope powered at ten kilovolts, employing back-scattering electron imaging. The nodules are generally smooth and tend to be oblong rather than spherical, yet are generally uniform in average diameter, in the range of about one to two microns, as is apparent from the white horizontal bar in the photograph indicating a length of ten microns. Pores or indentations between nodules likewise are approximately one or two microns in average diameter.

The nodules, indentations and other surface irregularities of course have virtually no impact on the geometric surface area, i.e. the exterior surface area of an identically sized electrode having a smooth exterior surface, which determines current density for stimulation. However, they have a substantial and surprising impact on the real surface area and the reactive surface area. In this context, the real surface area is the total fluid to metal interface, which includes interior surface areas along passageways as well as the exterior surface. The reactive surface area is the proportion of the real surface area available for converting electronic current to ionic current. For example, in an electrode having a 7.5 square mm profile, the real surface area is approximately 500 square mm. Further, comparison of electrode 20 with a similar packed wire electrode having no texturizing treatment yielded a fifteen-fold improvement in charge transfer, a seventy-eight percent reduction in polarization losses, and a seventy-four percent decrease in the after potential at the electrode interface, all indicative of substantially increased reactive surface area. Generally, the increase in reactive surface area has been found to be at least an order of magnitude, more particularly from ten to one hundred-fold.

In accordance with the present invention, electrode 20, particularly along the entire exposed outer surface of wire 28 and screen 30, is texturized or treated to provide multiple surface irregularities, thus to increase the surface area of the exposed outer surface by from one to two orders of magnitude. Surface texturizing is achieved by vapor deposition, magnetron sputtering, ion impregnation or similar type of process, for convenience broadly referred to as glow discharge processes, either alone or in combination with electroplating. In particular, a high energy, low temperature vapor deposition process, at an argon pressure of about one torr or less, has been found satisfactory in applying the layers necessary for texturizing wire 28 and screen 30.

One preferred approach is illustrated in FIG. 4, and involves forming surface irregularities by glow discharge or vapor deposition, after a wire such as wire 28 has been sintered. More particularly, an underlayer 38 of titanium is sputtered onto a wire 40 to a thickness of from 20,000 to about 35,000 Angstroms (2 to 3.5 microns). The primary purpose of underlayer 38 is to provide the desired texture, in the form of multiple nodules or adhering particles. The particles are somewhat elongate and irregular, but in general have average diameters ranging from one to two microns. Underlayer 38 also serves as an adhesion layer for a layer 42 of platinum. Platinum layer 42, sputtered to a thickness of approximately 15,000 to 20,000 Angstroms, is applied to reduce the activation energy and enhance biocompatibility. If desired, a thin outer layer 44 of carbon is sputtered onto the platinum layer, preferably to a thickness in the range of 1,500 to 2,000 Angstroms, to further enhance biocompatibility of the electrode.

FIG. 5 illustrates an alternative texturized filament in which a platinum wire 46 is coated by sputtering with an underlayer 48 of titanium to a thickness of approximately 8,000 Angstroms. In this alternative approach, titanium layer 48 is used only for adhesion. A platinum texturing layer 50 is then applied to the titanium layer in a process involving multiple platings of platinum-black, preferably in the range of from eight to fifteen applications for a thickness of 30,000 to 150,000 Angstroms. Following each electroplating of platinum-black, the electrode is baked at approximately 650 degrees C. for about twenty minutes, to enhance adhesion. The multiple applications result in a texture for the platinum-black layer in the form of multiple particles or nodules, again with average diameters equal to or less than two microns.

FIG. 6 illustrates yet another approach, in which the first layer applied to a platinum wire 52 by vapor deposition, is an underlayer 54 approximately 8,000 Angstroms thick, preferably of titanium. Underlayer 54 is provided principally to ensure proper adhesion of the next subsequent layer, a texturizing layer 56 preferably aluminum. Layer 56 is applied by vapor deposition over the titanium underlayer to a thickness of approximately 40,000 Angstroms. The aluminum, when so applied, forms multiple nodules or adhering particles. The particles are somewhat elongate and irregular, but generally have average diameters of from one to two microns. The aluminum texture layer is deposited in an argon or other inert gas atmosphere, thus to form multiple indentations about one micron in diameter for further texturizing the aluminum layer.

Following aluminum deposition, a platinum layer 58 is applied over the aluminum layer by vapor deposition, to a thickness of approximately 20,000 Angstroms. While platinum and platinum-black are preferred, this layer may be formed of platinum, iridium, ruthenium or alloys or compounds of these constituents, their salient characteristics being a catalytic nature and low activation energy.

Finally, although not essential, a cover layer 60 of carbon may be applied over the outer platinum layer, to a thickness in the range of from 1,500 to 2,000 Angstroms, to further enhance the biocompatibility of the electrode.

FIG. 7 shows an intermediate portion along the length of an intravascular lead 62 including a conductor coil 64 contained within a dielectric sheath 66. Also surrounding the coil and interrupting the continuity of sheath 66 is a ring electrode 68 including a platinum wire 70 packed into an annular configuration between an outer wire mesh screen 72 and an electrically conductive tube 74. Wire 70 is treated to enhance its surface texture in the same manner as wire 28 of electrode 20. Alternatively, a perforated or slotted outer casing may contain wire 70. Again, surface texturizing is accomplished after initial formation of the electrode, including sintering as previously described.

FIG. 8 and 9 show a patch electrode 76 used in defibrillation or cardioversion, formed by interwoven, mutually perpendicular strands of platinum or titanium wire 78 and 80, and a conductor 82 for transmitting electrical signals to and from electrode 76. As seen from FIG. 9, patch electrode 76 may include several levels of perpendicular strands, with a finer, stretched and packed platinum wire 84 contained between separate layers, and microtexturized over exterior and interior surfaces as described above.

Thus, in accordance with the present invention a variety of body implantable electrodes are formed with a combined macro porosity and micro testurizing, for a substantial increase in reactive surface area, enhanced ingrowth of tissue for improved electrode stabilization, and reduced interface impedance. Polarization loss is markedly reduced to improve signal quality, and shorten the refractory period after a stimulating pulse is reduced to enable a more rapid sensing of tissue response

What is claimed is:

1. An electrode implantable inside a patient, comprising:
    an electrode body constructed of an electrically conductive filament structure including a plurality of elongate fiber elements with diameters of at least five microns, said fiber elements bundled in close proximity with one another and forming multiple passages throughout the electrode body and open to the exterior of the body, whereby an exposed surface of the electrode body includes an exterior surface portion, and an interior surface portion along and defining said passages, with the volume occupied by the passages comprising more than one half of the total volume occupied by the electrode body; and
    a surface texture comprising multiple surface irregularities formed over substantially the entire exposed surface of the electrode body, thereby to substantially increase the surface area of said exposed surface as compared to an equivalent smooth surface of an identically sized electrode body.

2. The implantable electrode of claim 1 wherein:
at least some of the passages have diameters in the range of from ten to fifty microns, and the surface area of said exposed surface is greater than an equivalent smooth surface of an equally sized electrode body, by a factor of at least ten.

3. The implantable electrode of claim 2 wherein:
said filament structure includes at least one strand of a metallic wire packed into a compress.

4. The implantable electrode of claim 3 wherein:
said filament structure is a single strand of said metallic wire, said fiber elements comprising portions of the single strand.

5. The electrode of claim 3 wherein:
said irregularities are formed as a metallic texturizing layer applied to said metallic wire.

6. The electrode of claim 5 wherein:
said metallic texturizing layer consists essentially of aluminum.

7. The electrode of claim 5 wherein:
said metallic texturizing layer consists essentially of platinum.

8. The electrode of claim 5 wherein:
said metallic texturizing layer consists essentially of titanium.

9. The electrode of claim 5 wherein:
said texturizing layer is applied by vapor deposition following the formation of said compress.

10. The electrode of claim 5 further including:
an adhesion enhancing underlayer between said metallic wire and said texturizing layer.

11. The electrode of claim 10 wherein:
said underlayer consists essentially of titanium.

12. The electrode of claim 5 further including:
an inert metallic cover layer over said metallic texturizing layer.

13. The electrode of claim 12 wherein:
said cover layer is formed of a catalytic material having a low activation energy.

14. The electrode of claim 13 wherein:
said catalytic material consists essentially of one of the following constituents: platinum, titanium, and a platinum-iridium alloy.

15. The electrode of claim 14 wherein:
said catalytic material consists essentially of platinum.

16. The electrode of claim 15 further including:
a carbon layer vapor deposited over said platinum layer.

17. The electrode of claim 3 wherein:
said irregularities include multiple nodules having average diameters of less than about four microns.

18. The electrode of claim 17 wherein:
the average diameter of said nodules is from one to two microns.

19. The electrode of claim 18 wherein:
said irregularities further include depressions having an average diameter of about one to two microns.

20. The electrode of claim 1 wherein:
said passages have average diameters in the range of from about ten microns to about one hundred fifty microns.

21. The electrode of claim 20 wherein:
said passages have average diameters in the range of from ten to fifty microns.

22. An intravascular cardiac pacing lead implantable inside a patient, including:
an electrode body constructed of an electrically conductive filament structure including a plurality of elongate fiber elements with diameters of at least five microns, said fiber elements being bundled in close proximity with one another and forming multiple passages throughout the electrode body and open to the exterior of the body, whereby an exposed body and open to the exterior of the body, whereby an exposed surface of the electrode body includes an exterior surface portion, and an interior surface portion disposed along and defining the passages, at least some of the passages having diameters in the range of ten to fifty microns, with the volume occupied by the passages comprising more than one half of the total volume occupied by the electrode body;

a surface texturing comprising multiple surface irregularities formed over substantially the entire exposed surface of the electrode body, in sufficient size and density to provide an enlarged surface area of said exposed surface, as compared to an equivalent smooth surface of an identically sized electrode body, by a factor of at least five;

a flexible electrical conductor and a flexible, biocompatible, dielectric sheath surrounding said conductor along substantially the entire length thereof; and a coupling means for electrically and mechanically joining the electrode body with respect to a distal end of the conductor, said electrode body being joined to and substantially covering a distal end of the coupling means.

23. A defibrillation patch electrode comprising:
a first layer of interwoven, mutually perpendicular strands formed of a biocompatible, electrically conductive material;

a second layer comprised of an electrically conductive filament structure contained against said first layer, said filament structure including a plurality of elongate fiber elements with diameters of at least five microns, bundled in close proximity to one another and forming multiple passages open to said first layer, an exposed surface of the filament structure including an exterior surface portion, and an interior surface portion along and defining the passages, with the volume occupied by the passages comprising more than one half of the total volume occupied by the second layer; and a surface texture comprising multiple surface irregularities formed over substantially the entire exposed surface of said filament structure, said irregularities being of sufficient size and density to provide an enhanced surface area of said exposed surface, as compared to the area of an equivalent smooth surface of an identically sized filament structure, by a factor of at least five.

24. The defibrillation patch electrode of claim 23 further including:
a third layer of interwoven, mutually perpendicular strands formed of a biocompatible, electrically conductive material disposed opposite said first layer, with said second layer contained between the first and third layers.

25. The defibrillation patch electrode of claim 24 wherein:
at least some of the passages have diameters in the range of from ten to one hundred and fifty microns.

26. An implantable device for sensing electrical activity in body tissue, including:

an electrode body positionable at a select area of body tissue, said electrode body constructed of an electrically conductive filament structure including multiple elongate fiber elements having diameters of at least five microns and bundled in close proximity with one another to form multiple passages throughout the electrode body and open to the exterior of the electrode body, whereby an exposed surface of the filament structure includes an exterior surface portion and an interior surface portion along and defining said passages, with the volume occupied by the passages comprising more than one half of the total volume occupied by the filament structure;

a surface texture comprising multiple surface irregularities formed over substantially the entire exposed surface of the filament structure, in sufficient size and density to provide an enhanced surface area of said exposed surface, as compared to the surface of an equivalent smooth surface of an equally sized filament structure, by a factor of at least five; and a conductor electrically associated with said electrode body for transmitting electrical pulses from said selected area of body tissue to a sensing location remote from the selected area.

27. The implantable device of claim 26, wherein:
at least some of the passages have diameters in the range from ten to one hundred and fifty microns.

* * * * *

UNITED STATES PATENT AND TRADEMARK OFFICE
CERTIFICATE OF CORRECTION

PATENT NO. : 5,074,313

DATED : December 24, 1991

INVENTOR(S) : Roger W. Dahl and Sanjiv Arora

It is certified that error appears in the above-identified patent and that said Letters Patent is hereby corrected as shown below:

Column 10, Lines 5 and 6 of Claim 22, please delete the phrase "whereby an exposed body and open to the exterior of the body,".

Signed and Sealed this

Sixth Day of April, 1993

*Attest:*

STEPHEN G. KUNIN

*Attesting Officer*     *Acting Commissioner of Patents and Trademarks*